(12) United States Patent
Kato et al.

(10) Patent No.: US 9,151,728 B2
(45) Date of Patent: Oct. 6, 2015

(54) GAS SENSOR

(75) Inventors: Hidekazu Kato, Ichinomiya (JP); Tatsuya Okumura, Kani (JP); Masahiro Asai, Nagoya (JP); Tomoyuki Miyashita, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 3 days.

(21) Appl. No.: 13/575,494

(22) PCT Filed: Dec. 6, 2011

(86) PCT No.: PCT/JP2011/006826
§ 371 (c)(1),
(2), (4) Date: Jul. 26, 2012

(87) PCT Pub. No.: WO2012/107980
PCT Pub. Date: Aug. 16, 2012

(65) Prior Publication Data
US 2012/0304735 A1    Dec. 6, 2012

(30) Foreign Application Priority Data

Feb. 7, 2011 (JP) .................................. 2011-024120

(51) Int. Cl.
*G01N 7/00* (2006.01)
*G01N 27/406* (2006.01)

(52) U.S. Cl.
CPC ................................ *G01N 27/4062* (2013.01)

(58) Field of Classification Search
CPC . G01F 23/2962; G01F 23/284; G01F 23/296; G01F 23/2961; G01R 3/00; H01L 2924/00014; H01L 2224/48091; H01L 2924/10253; C08L 67/04; C08L 2666/02; C08L 69/00; G01N 27/4077; G01N 27/127; G01N 27/126; G01N 27/414; G01N 27/4141; G01N 27/4062

USPC ......... 73/23.2, 23.31, 31.05, 31; 29/595, 619, 29/758

See application file for complete search history.

(56) References Cited

U.S. PATENT DOCUMENTS

| 5,651,285 A | * | 7/1997 | Legras ......................... 73/290 V |
| 6,073,492 A | * | 6/2000 | Rosselson et al. .............. 73/644 |

(Continued)

FOREIGN PATENT DOCUMENTS

| JP | 2002-39985 A | 2/2002 | |
| JP | 2002039985 A | * 2/2002 | ........... G01N 27/409 |

(Continued)

OTHER PUBLICATIONS

International Search Report for PCT/JP2011/006826 dated Jan. 10, 2012.

*Primary Examiner* — Peter Macchiarolo
*Assistant Examiner* — Mohammed Keramet-Amircola
(74) *Attorney, Agent, or Firm* — Sughrue Mion, PLLC

(57) ABSTRACT

Provided is a gas sensor in which a connection terminal can be favorably fitted onto a cylindrical sensor element without causing a breakage of the connection terminal. An oxygen sensor (1) includes an outer connection terminal (29) having an outer fitting portion (53), an extension portion (55) extending inwardly from an axially intermediate point of the outer fitting portion (53) and pulling prevention portions (75) and (77) formed on rear end parts of the outer fitting portion (53) at positions adjacent to the extension portion (55). When the extension portion (55) of the outer connection terminal (29) is inserted in and pulled out from a through hole (23) of a separator (27), the extension portion (55) can be prevented from further pulling in the through hole (23) by contact of the pulling prevention portions (75) and (77) with a front end surface of the separator (27).

9 Claims, 15 Drawing Sheets

(56) References Cited

U.S. PATENT DOCUMENTS

| | | | |
|---|---|---|---|
| 7,424,819 B2 * | 9/2008 | Fujita et al. | 73/31.05 |
| 2004/0011126 A1 * | 1/2004 | Otto et al. | 73/290 R |
| 2004/0168514 A1 * | 9/2004 | Tsukada et al. | 73/290 V |
| 2006/0000274 A1 * | 1/2006 | Kallsand et al. | 73/290 V |
| 2007/0205114 A1 * | 9/2007 | Mathur | 205/792 |
| 2007/0209434 A1 * | 9/2007 | Peters | 73/290 V |
| 2007/0243760 A1 * | 10/2007 | Fujita et al. | 439/585 |
| 2011/0100118 A1 * | 5/2011 | Tsukada et al. | 73/290 V |

FOREIGN PATENT DOCUMENTS

| | | | |
|---|---|---|---|
| JP | 2007-285769 A | | 11/2007 |
| JP | 2007285769 A | * | 11/2007 |
| JP | 2008-286731 A | | 11/2008 |
| JP | 2008286731 A | * | 11/2008 |
| JP | 2008-298535 A | | 12/2008 |
| JP | 2008298535 A | * | 12/2008 |

* cited by examiner (a)

(b)

(a)

(b)

GAS SENSOR

CROSS REFERENCE TO RELATED APPLICATIONS

This application is a National Stage of International Application No. PCT/JP2011/006826 filed Dec. 6, 2011, claiming priority based on Japanese Patent Application No. 2011-024120 filed Feb. 7, 2011, the contents of all of which are incorporated herein by reference in their entirety.

TECHNICAL FIELD

The present invention relates to a gas sensor having a cylindrical sensor element, a connection terminal fitted onto the sensor element and a separator formed with a through hole into which a part of the connection terminal is inserted.

BACKGROUND ART

For example, an oxygen sensor for measuring the concentration of oxygen in automotive exhaust gas is conventionally known as a sensor having a sensor element to detect a gas under measurement. There is known a sensor element for use in such an oxygen sensor, which includes a bottomed cylindrical solid electrolyte body, an inner electrode formed on an inner surface of the solid electrolyte body and an outer electrode formed on an outer surface of the solid electrolyte body, as disclosed in Patent Documents 1 and 2.

An inner connection terminal is fitted into a rear end portion of the sensor element and electrically connected to the inner electrode. A sensor output lead is connected to a rear end portion of the inner connection terminal. A rod-shaped ceramic heater is inserted in the sensor element such that the inner connection terminal is attached around the ceramic heater.

Further, an outer connection terminal (ground connection terminal) is fitted onto the rear end portion of the sensor element and electrically connected to the outer electrode. A ground lead is connected to a rear end portion of the outer connection terminal.

As shown in FIG. 14(a), the outer connection terminal P1 generally includes a cylindrical outer fitting portion P4 (having left and right curved wing sections P2 and P3) brought into contact with the sensor element from outside and an elongated extension portion P5 extending from a point midway between the left and right wing sections P2 and P3 on an axially upper end of the outer fitting portion P4.

As the lead is connected to an upper end of the extension portion P5 of the outer connection terminal P1, the extension portion P5 is in the form of protruding toward the side on which both of the wing sections P2 and P3 project (toward the inside) and then extending axially upwardly (toward the upper side in the drawing) so that the extension portion P5 can be offset according to the position of the lead. Further, the outer connection terminal P1 is arranged in such a manner that the extension portion P5 passes through a through hole P7 of a ceramic separator P6 as shown in FIG. 14(b).

PRIOR ART DOCUMENTS

Patent Document

Patent Document 1: Japanese Laid-Open Patent Publication No. 2007-285769

Patent Document 2: Japanese Laid-Open Patent Publication No. 2008-286731

SUMMARY OF THE INVENTION

Problems to be Solved by the Invention

The above-mentioned oxygen sensor is manufactured by assembling the outer connection terminal P1 and the separator P6 into one unit (called an intermediate assembly unit) upon insertion of the extension portion P5 of the outer connection terminal P1 into the through hole P7 of the separator P6, and then, fitting the outer connection terminal P1 onto the sensor element with the use of an automechanism. At this time, there arise the following problems.

When the outer connection terminal P1 and the separator P6 are assembled together, the extension portion P5 of the outer connection terminal P1 is inserted into the through hole P7 of the separator 6 from one end thereof and pulled out from the other end of the through hole P7. If the extension portion P5 is pulled out excessively, not only a bottom section of the extension portion P5 but also a part of the outer fitting portion P4 located around the extension portion P5 are fitted in the through hole P7 so that the outer fitting portion P4 tilts as shown in FIG. 15(a).

In such a state that the outer fitting portion P4 tilts with respect to the axial direction of the separator P6, the outer connection terminal P1 cannot be fitted (together with the separator P6) favorably onto the sensor element P8 as shown in FIG. 15(b). This can result in a breakage of the outer fitting portion P4 as shown in FIG. 15(c).

The present invention has been made in order to solve the above problems. It is accordingly an object of the present invention to provide a gas sensor in which a connection terminal can be favorably fitted onto a cylindrical sensor element without causing a breakage of the connection terminal.

Means for Solving the Problems (1) According to a first aspect of the present invention, there is provided a gas sensor, comprising: a cylindrical sensor element; a connection terminal extending axially of the sensor element and brought into contact with an outer surface of the sensor element; and a separator located rear of the sensor element and having a through hole in which a rear end side of the connection terminal is inserted, wherein the connection terminal has: a cylindrical outer fitting portion formed on a front end side of the connection terminal and fitted onto the sensor element; an extension portion extending rearward from the outer fitting portion and inserted in the through hole of the separator; and a pulling prevention portion adapted to prevent the extension portion from further pulling in the through hole by contact with a front end surface of the separator.

In the first aspect of the present invention, the pulling prevention portion is formed on the connection terminal so as to prevent further pulling of the extension portion into the through hole by contact with the front end surface of the separator (the surface of the side of the separator on which the sensor element is situated). It is therefore possible to, when the extension portion of the connection terminal is inserted in the through hole of the separator from one end thereof and pulled out from the other end of the through hole during assembling of the connection terminal and the separator, prevent the extension portion from further pulling in the through hole by contact of the pulling prevention portion with the front end surface of the separator.

(2) According to a second aspect of the present invention, the gas sensor is characterized in that: the extension portion is formed to protrude inwardly from an axially intermediate point of the outer fitting portion; and the pulling prevention portion is formed on a rear end part of the outer fitting portion at a position adjacent to the extension portion so as to prevent the extension portion from further pulling in the through hole by contact with the front end surface of the separator.

In the second aspect of the present invention, the extension portion of the connection terminal is formed in such a manner as to protrude inwardly from the axially intermediate point of the outer fitting portion; and the pulling prevention portion is formed on the rear end part of the outer fitting portion at the position adjacent to the extension portion so as to prevent further pulling of the extension portion into the through hole by contact with the front end surface of the separator as shown in FIG. 1(a) and FIG. 1(b).

It is therefore possible to, when the extension portion of the connection terminal is inserted in the through hole of the separator from one end thereof and pulled out from the other end of the through hole during assembling of the connection terminal and the separator, prevent the extension portion from further pulling in the through hole by contact of the end part of the outer fitting portion (that is, the pulling prevention portion) with the front end surface of the separator.

(3) According to a third aspect of the present invention, the gas sensor is characterized in that: the pulling prevention portion is formed on a rear end part of the outer fitting portion at a position adjacent to the extension portion so as to protrude outwardly from the outer fitting portion and prevent the extension portion from further pulling in the through hole by contact with the front end surface of the separator.

In the third aspect of the present invention, the pulling prevention portion is formed on the rear end part of the outer fitting portion of the connection terminal at the position adjacent to the extension portion so as to protrude outwardly from the outer fitting portion and prevent further pulling of the extension portion into the through hole by contact with the front end face of the separator as shown in FIG. 1(c).

It is therefore possible to, when the extension portion of the connection terminal is inserted in the through hole of the separator from one end thereof and pulled out from the other end of the through hole during assembling of the connection terminal and the separator, prevent the extension portion from further pulling in the through hole by contact of the pulling prevention portion, which is formed on the outer fitting portion, with the front end surface of the separator.

(4) According to a fourth aspect of the present invention, the gas sensor is characterized in that: the pulling prevention portion is formed on the extension portion so as to protrude outwardly from the extension portion and prevent the extension portion from further pulling in the through hole by contact with the front end surface of the separator.

In the fourth aspect of the present invention, the pulling prevention portion is formed on the extension portion of the connection terminal so as to protrude outwardly from the extension portion and prevent further pulling of the extension portion into the through hole by contact with the front end surface of the separator as shown in FIG. 1(d).

It is therefore possible to, when the extension portion of the connection terminal is inserted in the through hole of the separator from one end thereof and pulled out from the other end of the through hole during assembling of the connection terminal and the separator, prevent the extension portion from further pulling in the through hole by contact of the pulling prevention portion, which is formed on the extension portion, with the front end surface of the separator.

(5) According to a fifth aspect of the present invention, the gas sensor is characterized in that: the extension portion protrudes in a direction inclined inwardly with respect to an axial direction of the outer fitting portion.

(6) According to a sixth aspect of the present invention, the gas sensor is characterized in that: the extension portion includes a bottom part extending in an axial direction of the outer fitting portion and another part extending from the bottom part in a direction inclined inwardly with respect to the axial direction.

(7) According to a seventh aspect of the present invention, the gas sensor is characterized in that: a position at which the extension portion protrudes inwardly from the outer fitting portion is located rear of an axially center position of the outer fitting portion.

(8) According to an eighth aspect of the present invention, the gas sensor is characterized in that: cuts are formed axially in a rear end side of the outer fitting portion on opposite sides of the extension portion with respect to a radial direction (i.e. along a circumferential direction of the cylindrical outer fitting portion).

In the above-mentioned aspects of the present invention, the term "front" refers to the side on which the sensor element is situated (the side on which the gas under measurement is detected); and the term "rear" refers to the side on which the separator is situated. Further, the term "inner" refers to the side closer to the center of the cylindrical component such as sensor element or outer fitting portion; and the term "outer" refers to the side opposite to the inner side.

Effects of the Invention

In the first aspect of the present invention, the outer fitting portion does not tilt with respect to the axial direction of the separator. The connection terminal can be thus favorably fitted onto the sensor element without causing a breakage of the connection terminal in the subsequent process step.

In the second aspect of the present invention, the outer fitting portion does not tilt with respect to the axial direction of the separator. The connection terminal can be thus favorably fitted onto the sensor element without causing a breakage of the connection terminal in the subsequent process step.

In the third aspect of the present invention, the outer fitting portion does not tilt with respect to the axial direction of the separator. The connection terminal can be thus favorably fitted onto the sensor element without causing a breakage of the connection terminal in the subsequent process step.

In the fourth aspect of the present invention, the outer fitting portion does not tilt with respect to the axial direction of the separator. The connection terminal can be thus favorably fitted onto the sensor element without causing a breakage of the connection terminal in the subsequent process step.

In the fifth aspect of the present invention, the extension portion protrudes in the direction inclined inwardly with respect to the outer fitting portion so as to perform the spring function. This leads to an advantage that, even when the extension portion is pulled rearward, a breakage is unlikely to occur in the base section of the extension portion. This also allows the outer fitting portion to be located radially outside of the extension portion and thereby makes it easier to, in the case where the pulling prevention portion is formed on the outer fitting portion, bring the pulling prevention portion into contact with the front end surface of the separator.

In the sixth aspect of the present invention, the bottom part of the extension portion extends in the axial direction of the outer fitting portion; and the other part of the extension portion extends from the bottom part in the direction inclined inwardly with respect to the axial direction. This leads to an advantage that, even when the extension portion is pulled rearward, a breakage is unlikely to occur in the base section of the extension portion.

In the seventh aspect of the present invention, the position of protrusion of the extension portion is located rear of the axially center position of the outer fitting portion. This leads to an advantage that the extension portion is unlikely to interfere with fitting of the connection terminal onto the sensor element. This also makes it possible to increase the amount of fitting of the connection terminal onto the sensor element and secure the stable fixing of the connection terminal and the sensor element.

In the eighth aspect of the present invention, the cuts are formed on the opposite sides of the extension portion. This makes it possible to separate the extension portion and the outer fitting portion from each other by the cuts and, by bending such a separated extension portion inwardly, allows the extension portion to protrude inwardly (e.g. in an inclined manner) from the axially intermediate point of the outer fitting portion.

DESCRIPTION OF EMBODIMENTS

Exemplary embodiments of the present invention will be described below with reference to the drawings.

First Embodiment

The present embodiment specifically refers to, as a gas sensor, an oxygen sensor for detecting the concentration of oxygen in exhaust gas of an automotive vehicle.

a) The oxygen sensor of the present embodiment will be first described below with reference to FIGS. 2 and 3. It is herein noted that: the lower and upper sides in FIGS. 2 and 3 correspond to front and rear sides of the oxygen sensor, respectively.

Figure 1:
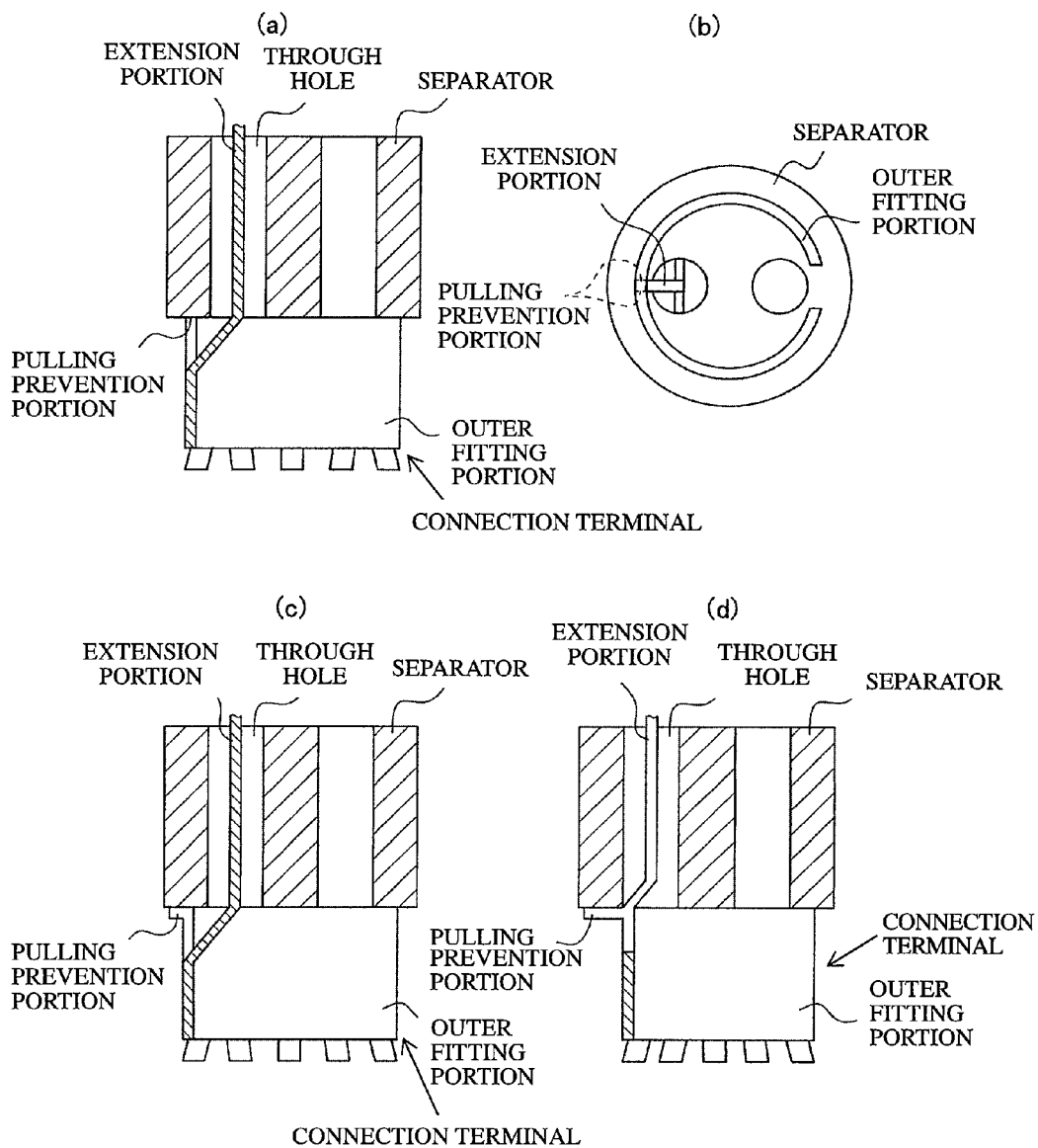
FIG. 1(a) is a vertical cross-sectional view schematically showing a separator and a connection terminal of a gas sensor according to a second aspect of the present invention.
FIG. 1(b) is a schematic view of the Separator and the connection terminal when viewed from a front end side.
FIG. 1(c) is a vertical cross-sectional view schematically showing a separator and a connection terminal of a gas sensor according to a third aspect of the present invention.
FIG. 1(d) is a vertical cross-sectional view schematically showing a separator and a connection terminal of a gas sensor according to a fourth aspect of the present invention.
Figure 2:
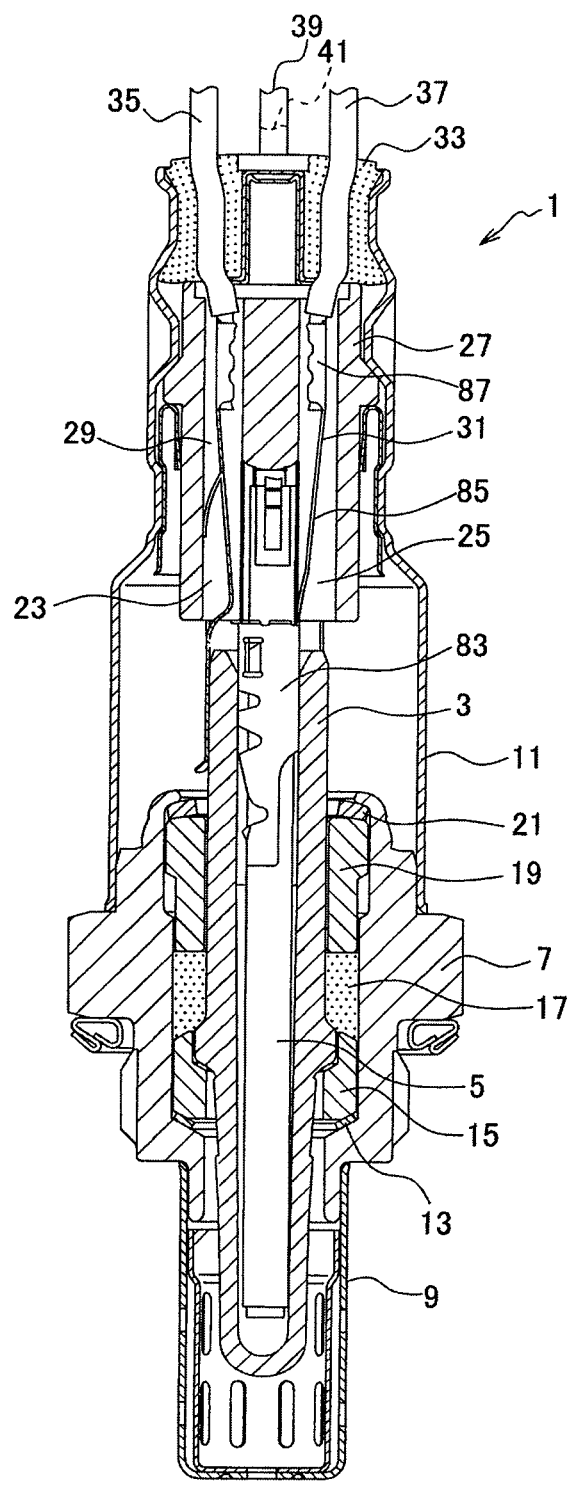
FIG. 2 is an axially cutaway schematic view of an oxygen sensor according to a first embodiment of the present invention.

Referring to FIG. 2, the oxygen sensor 1 of the present embodiment includes a narrow cylindrical sensor element 3 having a closed front end, a cylindrical column-shaped ceramic heater 5 inserted in the sensor element 3, a cylindrical metal shell 7 through which the sensor element 3 is inserted and fixed, a cylindrical metallic protector 9 coaxially fixed to a front end portion of the metal shell 7 and a cylindrical metallic outer tube 11 coaxially fixed to a rear end portion of the metal shell 7. For example, the ceramic heater 5 has an alumina body and a heating resistor.

For fixing and gas sealing of the sensor element 3, a metallic packing 13, a ceramic supporting member 15, a filling member 17 of talc powder, a ceramic sleeve 19 and a metallic gasket 21 are arranged between the sensor element 3 and the metal shell 7 in this order from the front side.

A ceramic separator 27 with a plurality of through holes 23 and 25 is arranged on a rear end portion of the sensor element 3. Metallic outer and inner connection terminals 29 and 31 are inserted in the through holes 23 and 25, respectively, for electrical connection to the sensor element 3. A grommet 33 of fluorocarbon resin is sealed in a rear end of the outer tube 11. Leads 35, 37, 39 and 41 are passed through the grommet 33 such that the leads 35 and 37 are connected to the outer and inner connection terminals 29 and 31 and such that the leads 39 and 41 are connected to the ceramic heater 5.

These leads 35 to 41 are electrically connected to a sensor control unit and an electrical control unit (ECU) of the automotive vehicle, both of which are situated apart from the oxygen sensor 1, although not shown in the drawings.

Hereinafter, the main sensor structural components will be described below in more detail.

Figure 3:
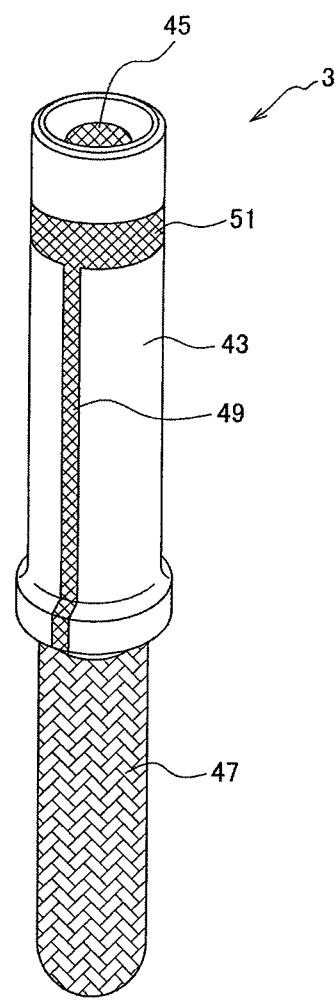
FIG. 3 is a perspective view of a sensor element of the oxygen sensor.

As shown in FIG. 3, the sensor element 3 has a bottomed cylindrical base body 43 formed of solid electrolyte containing zirconia as a main constituent. An inner electrode (reference electrode) 45 is formed of Pt or Pt alloy on substantially the whole of an inner circumferential surface of the base body 43. The inner connection terminal 31 is in contact with the inner electrode 45.

On the other hand, a porous outer electrode (detection electrode) 47 is formed of Pt or Pt alloy on a front end part of an outer circumferential surface of the base body 43 such that the whole of the front end part of the outer circumferential surface of the base body 43 is covered with the outer electrode 47. An electrode lead portion 49 is formed to extend rearward from the outer electrode 47. An annular electrode portion 51 is formed to be connected with the electrode lead portion 49. The outer connection terminal 29 is in contact with the annular electrode portion 51. Further, a porous electrode layer of heat-resistant ceramic material (not shown) is formed on a surface of the outer electrode 47 in order to protect the outer electrode 47 from poisoning by the exhaust gas.

Figure 4:
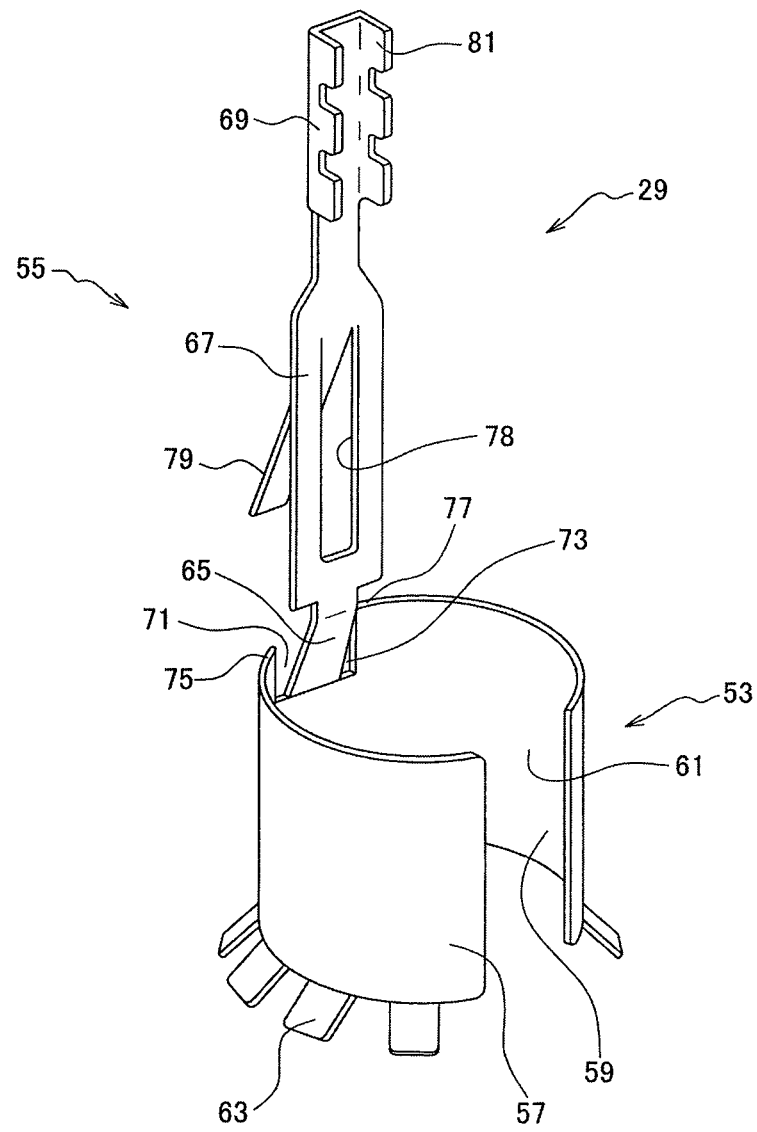
FIG. 4 is a perspective view of an outer connection terminal of the oxygen sensor.
Figure 5:
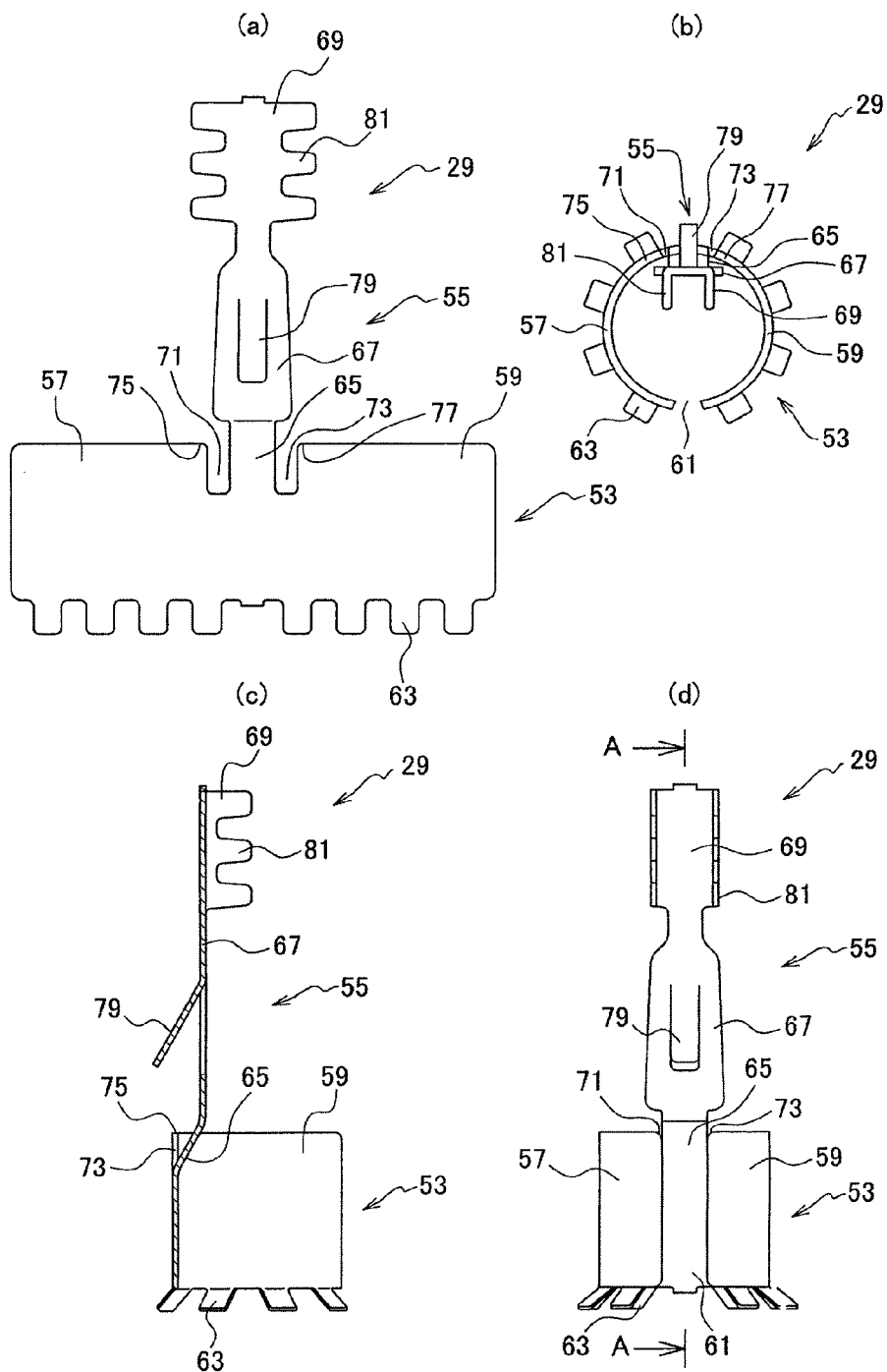
FIG. 5(a) is an exploded view of the outer connection terminal.
FIG. 5(b) is a plan view of the outer connection terminal.
FIG. 5(c) is a section view of the outer connection terminal taken along line A-A in FIG. 5(d)
FIG. 5(d) is a front view of the outer connection terminal.

As shown in FIGS. 4 and 5, the outer connection terminal 29 is an elongated ground terminal having a lower end side fitted onto the sensor element 3 and held in contact with the annular electrode portion 51 and an upper end side connected to the lead 35.

More specifically, the outer connection terminal 29 is formed by bending one metal plate of e.g. Inconel and includes an elastic cylindrical outer fitting portion 53 located on the lower end side thereof and an extension portion 55 extending axially upwardly from an upper end side of the outer fitting portion 53.

The outer fitting portion 53 has a pair of left and right wing sections 57 and 59 curved into arc shapes (when viewed in the axial direction). A gap (slit) 61 is provided between distal ends (radially distal ends) of the left and right wing sections 57 and 59 so as to separate the left and right wing sections 57 and 59 from each other in the axial direction. As the wing sections 57 and 59 are fitted on the sensor element 3 and fixed to the sensor element 3 by the action of their respective elastic forces, the inner diameter of the wing sections 57 and 59 is set slightly smaller than the outer diameter of the sensor element 3.

Further, a plurality of evenly spaced guide pieces 63 protrude diagonally outwardly from a lower end of the outer fitting portion 53 so that the outer connection terminal 29 can be easily fitted (guided without deviation from alignment) onto the sensor element 3.

The extension portion 55 has a plate-shaped bottom section 65 extending diagonally upwardly from the outer fitting portion 53 (more specifically, from a base end part of the left and right wing sections 57 and 59) in a direction inclined inwardly (e.g. inclined about 30° with respect to the axial direction), an intermediate section 67 extending axially upwardly from the bottom section 65 and a holding section 69 located upward of the intermediate section 67 and adapted to hold therein the lead 35.

As shown in the exploded view of FIG. 5(a), the bottom section 65 protrudes axially from a lower position than an upper end of the outer fitting portion 53. Namely, cuts 71 and 73 are formed axially in the upper end side of the outer fitting portion 53 on circumferentially opposite left and right sides of the bottom section 65 and thereby allow the bottom section 65 to protrude inwardly from an axially intermediate point of the outer fitting portion 65. The position of protrusion of the bottom section 65 is herein located upward of an axially center position of the outer fitting portion 53.

In the present embodiment, the bottom section 65 of the extension portion 55 protrudes inwardly from the axially intermediate point of the outer fitting portion 53 so that upper end parts of the outer fitting portion 53, which extend on the circumferentially opposite sides of the bottom section 65, are located outside of the bottom section 65 (when viewed from the axis center of the outer fitting portion 51). These upper end parts of the outer fitting portion 53 constitute pulling prevention portions 75 and 77 (to come into contact with a lower end of the separator 27 as will be explained later).

The radial width of a center part of the intermediate section 67 is widened. An axially elongated U-like shaped cut 78 is made in the center part of the intermediate section 67, thereby forming a rectangular protrusion piece 79. The protrusion piece 79 protrudes outwardly (such that a lower end side of the protrusion piece 79 extends more outwardly).

Three fixing pieces 81 are formed on each of left and right sides of the holding section 69 such that the lead 35 can be held by the fixing pieces 81.

Referring back to FIG. 2, the inner connection terminal 31 is an elongated sensor output terminal having a lower end side fitted into the sensor element 3 and held in contact with the inner electrode 45 and an upper end side connected to the lead 37.

The inner connection terminal 31 is formed by bending one metal plate of e.g. Inconel as in the case of the outer connection terminal 29. The inner connection terminal 31 includes a cylindrical inner fitting portion 83 located on the front end side thereof and fitted in the sensor element 3 so as to retain the ceramic heater 5 from outside. The inner connection terminal 31 also includes an elongated extension portion 85 extending rearward from a rear end of the inner fitting portion 83. A holding section 87 is formed on a rear end of the extension portion 58 and adapted to hold therein the lead 37.

Figure 6:
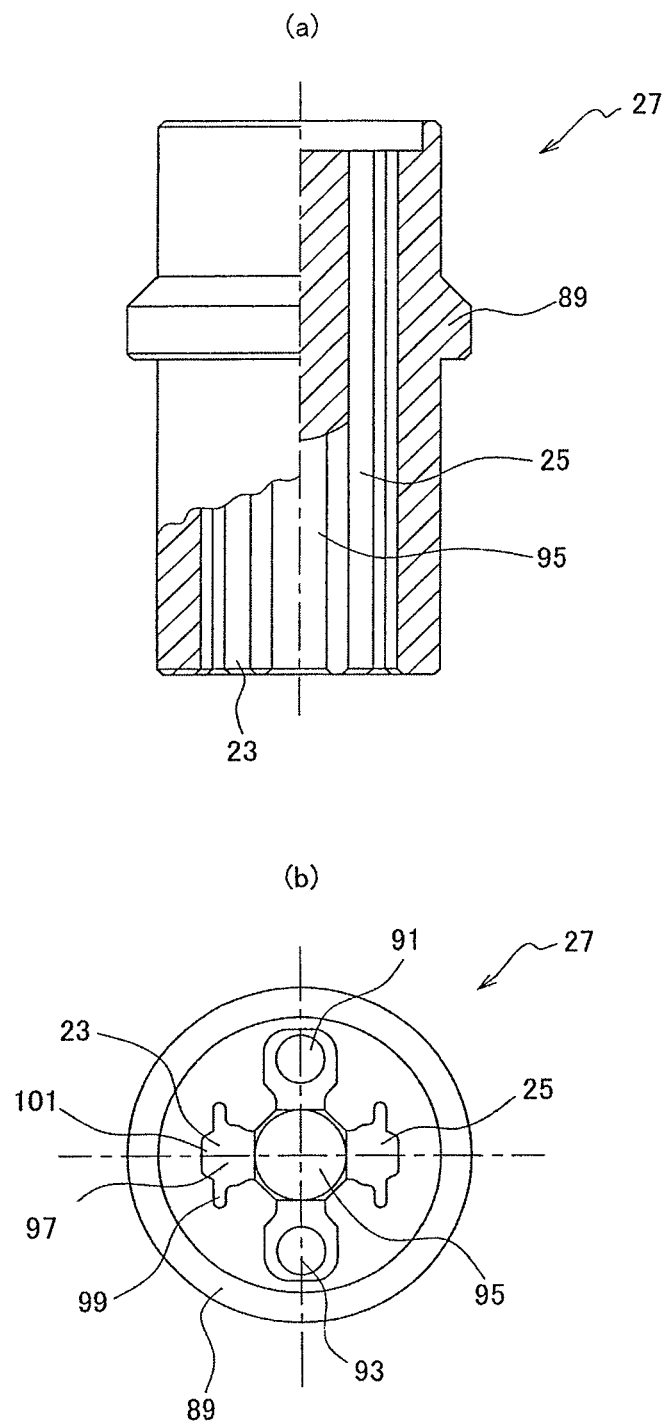
FIG. 6(a) is a partially cutaway front view of the separator.
FIG. 6(b) is a plan view of the separator.

As shown in FIG. 6, the separator 27 is a cylindrical member formed of electrically insulating alumina and includes a flange portion 89 formed on an outer circumferential surface thereof. The separator 27 has the above-mentioned pair of through holes 23 and 25 formed in the axial direction symmetrically with respect to the axis center, another pair of through holes 91 and 93 formed symmetrically with respect to the axis center (aligned perpendicular to the direction of arrangement of the through holes 23 and 25) and an elongated insertion hole 95 formed (with a closed rear end) along the axis center.

The intermediate section 67 and the holding section 69 of the outer connection terminal 29 are inserted in the through hole 23. As shown in FIG. 6(b), the through hole 23 includes a center hole region 97 having a substantially trapezoidal cross-section in a direction perpendicular to the axial direction, a slit region 99 extending in a slit-like manner from the center hole region 97 vertically in the drawing and a protruding hole region 101 protruding outwardly from the center hole region 97.

As will be explained later, the through hole 23 is formed such that the widened intermediate section 67 of the extension portion 55 is fitted in the slit region 99 and such that the protrusion piece 79 protruding from the intermediate section 67 is fitted in the protruding hole region 101. The through hole 25 is also formed into the same shape.

Figure 7:
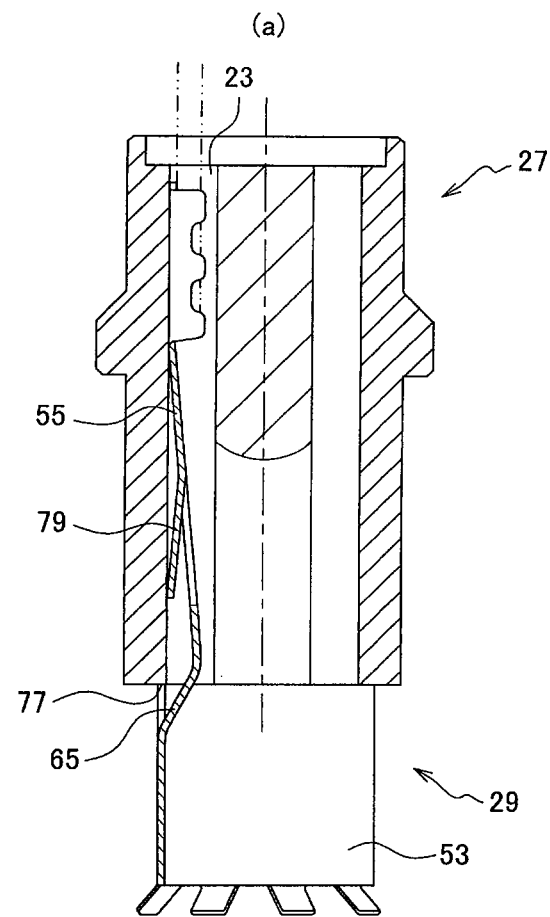
FIG. 7(a) is a cutaway schematic view showing an assembled state in which the outer connection terminal is assembled into the separator.
FIG. 7(b) is a bottom view showing the assembled state.
Figure 7:
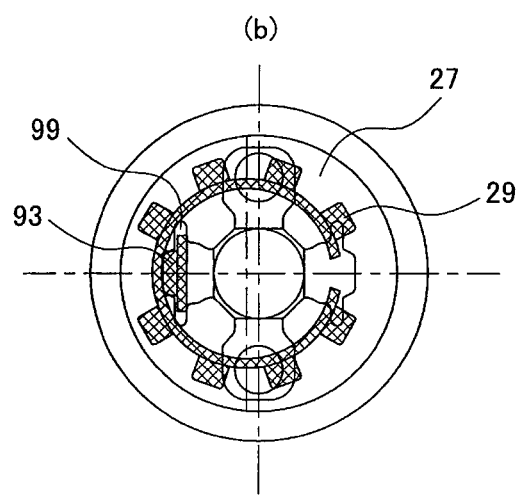

FIG. 7 shows a state in which the outer connection terminal 29 is assembled into the separator 27. In this assembled state, the upper end of the outer fitting portion 53 of the outer connection terminal 29 is brought into contact with the lower end of the separator 27; and the extension portion 55 of the outer connection terminal 29 is inserted through the through hole 23 of the separator 27.

The intermediate section 67 of the outer connection terminal 29 is substantially placed in position by insertion into the slit region 99 of the through hole 23. The protrusion piece 79 protruding from the intermediate section 67 is placed in the protruding hole region 101 of the through hole 23 so as to function as a leaf spring that pushes the outer connection terminal 29 inwardly and thereby prevents rattling of the outer connection terminal 29.

Figure 8:
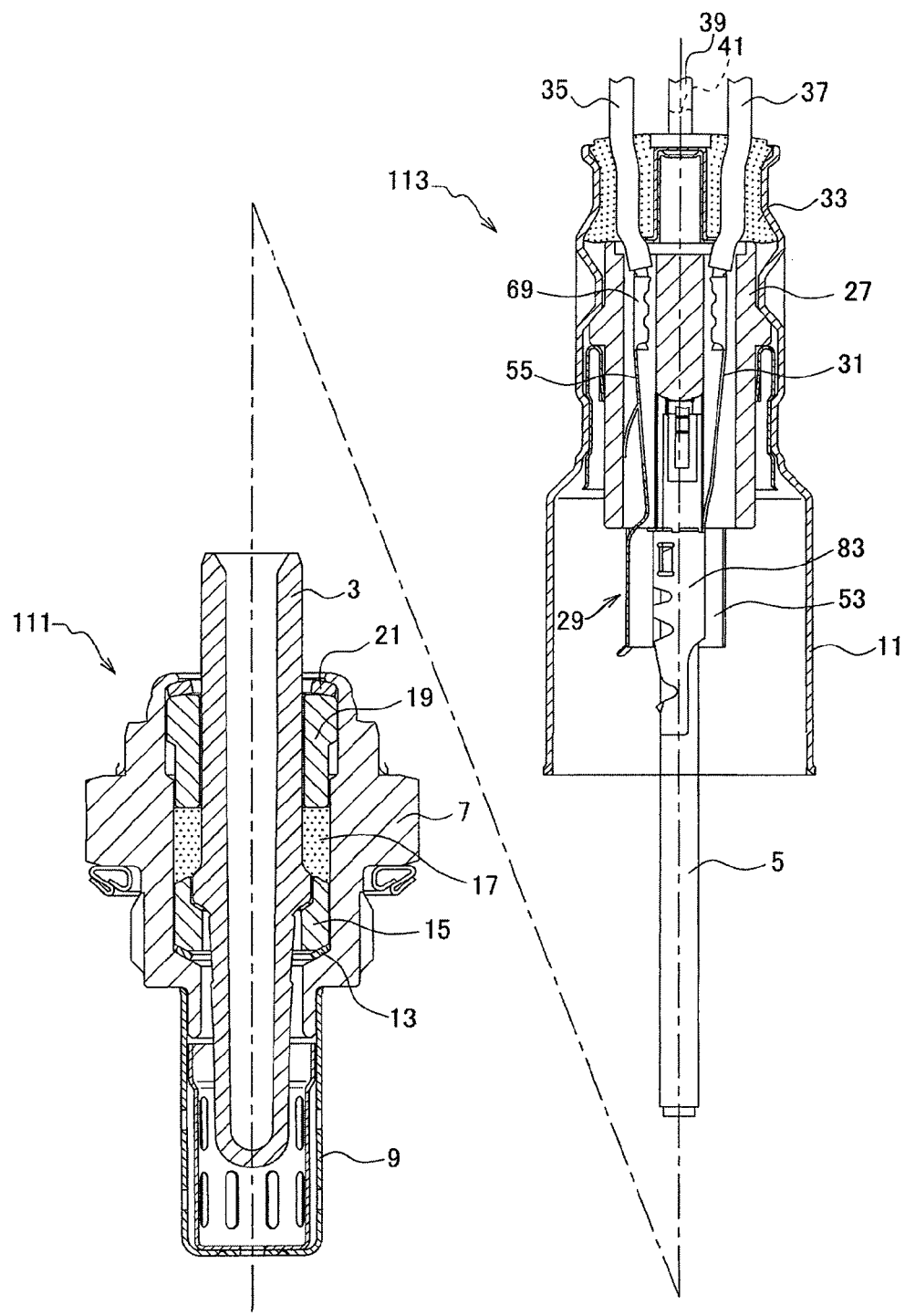
FIG. 8 is a schematic view showing a state in which the oxygen sensor is disassembled into two intermediate assembly units.

In the present embodiment, the pulling prevention portions 75 and 77 are formed on the opposite sides of the bottom section 65 of the (upwardly extending) extension portion 55, i.e., constituted by the upper end parts of the outer fitting portion 53 on the circumferentially opposite sides of the bottom section 65 as mentioned above. These pulling prevention portions 75 and 77 are located radially outside of a part of the extension portion 55 (corresponding in position to the upper end of the outer fitting portion 53) and brought into contact with the lower end surface of the separator 27. More specifically, the pulling prevention portions 75 and 77 come into contact with the loser end surface of the separator 27 at positions outside of the upper part of the inwardly protruding bottom section 65.

b) A manufacturing method of the gas sensor of the present embodiment will be next described below with reference to FIGS. 8 and 9. FIG. 8 shows the gas sensor after crimping of the grommet 33 and the like.

As shown in FIG. 8, a front intermediate assembly unit 111 is produced by joining the protector 9 to the front end portion of the metal shell 7 and fixing the sensor element 3 into the metal shell 7 by crimping, with the packing 13, the supporting member 15, the filling member 17, the sleeve 19 and the gasket 21 interposed therebetween.

The outer connection terminal 29 is cut out into a shape as shown in FIG. 4 by stamping the conductive plate material. At this time, the protrusion piece 79 of the intermediate section 67 is also cut out. The left and right wing sections 57 and 59 are formed by bending into the cylindrical shapes. Further, the guide pieces 63 of the wing sections 57 and 59, the fixing pieces 81 of the holding section 69 and the protrusion piece 79 of the intermediate section 67 are each formed by bending. With this, the outer connection terminal 29 is prepared.

After that, a core wire of the lead 35 is fixed by crimping to the holding section 69 of the outer connection terminal 29 as shown in FIG. 8. Similarly, the inner connection terminal 31 is prepared by stamping the plate material into a given shape and bending necessary parts of the plate material. A core wire of the lead 37 is fixed by crimping to the inner connection terminal 31. Then, the inner fitting portion 83 of the inner connection terminal 31 is fitted on and fixed to a rear end portion of the ceramic heater 5 from outside.

The outer connection terminal 29 to which the lead 35 is connected is placed, together with the inner connection terminal 31 and the ceramic heater 5, into the separator 27. More specifically, the extension portion 55 of the outer connection terminal 29 to which the lead 35 is connected, the extension portion 85 of the inner connection terminal 31 to which the lead 37 is connected and the rear end portion of the ceramic heater 5 (to which the leads 39 and 41 are connected) are placed into the separator 27.

Herein, the procedure for placing the above respective components in the separator 27 will be explained below in detail.

At the time of placing the parts of the outer connection terminal 29, the inner connection terminal 31 and the ceramic heater 5 in the separator 27, the leads 35 to 41 are pulled out toward the upper side in FIG. 8 through the through holes 23, 25, 91 and 93, respectively.

In more detail, the leads 39 and 41 connected to the ceramic heater 5 are passed through the respective through holes 91 and 93. The lead 35 connected to the outer connection terminal 29 is passed through the through hole 23. The lead 37 connected to the inner connection terminal 31 is passed through the through hole 25.

By holding the lead 37, the inner connection terminal 31 (retaining therein the ceramic heater 5) is pulled up until the rear end of the ceramic heater 5 comes into contact with the bottom of the insertion hole 95 of the separator 27.

On the other hand, the outer connection terminal 29 is pulled up by holding the lead 35 until the upper end parts of the outer fitting portion 53 of the outer connection terminal 29 (that is, the pulling prevention portions 75 and 77) conic into contact with the lower end of the separator 27 as shown in FIG. 7.

A rear intermediate assembly unit 113 is then produced, as shown in FIG. 8, by inserting the separator 27 in the outer tube 11, passing the leads 35 to 41 through the grommet 33 and fitting the grommet 33 in the rear end of the outer tube 11.

As explained above, the front intermediate assembly unit 111 in which the sensor element 3 and the like are retained in the metal shell 7 and the rear intermediate assembly unit 113 in which the outer connection terminal 29, the inner connection terminal 31, the ceramic heater 5 and the like are retained in the outer tube 11 are produced by the separate process steps.

The thus-obtained intermediate assembly units 111 and 113 are assembled together in such a manner that the axial direction of the intermediate assembly unit 111 agrees with the axial direction of the intermediate assembly unit 113. In the actual assembling process, the rear intermediate assembly unit 113 is placed below the front intermediate assembly unit 111 in contrast to FIG. 8 so that the front intermediate assembly unit 111 is attached from above to the rear intermediate assembly unit 113 with the use of an automechanism.

Figure 9:
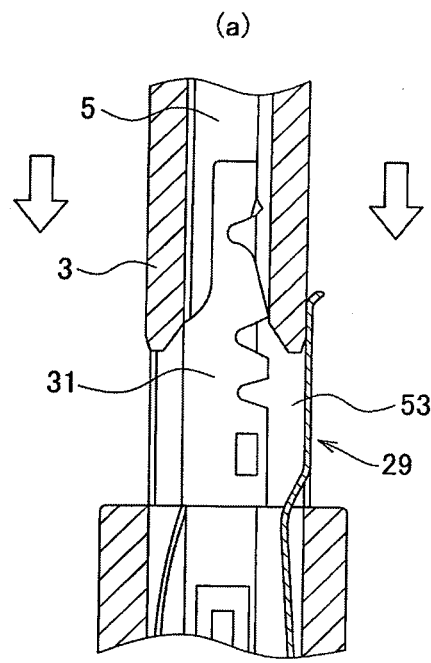
FIG. 9 is a schematic view showing a procedure for fitting the outer connection terminal onto the sensor element.
Figure 9:
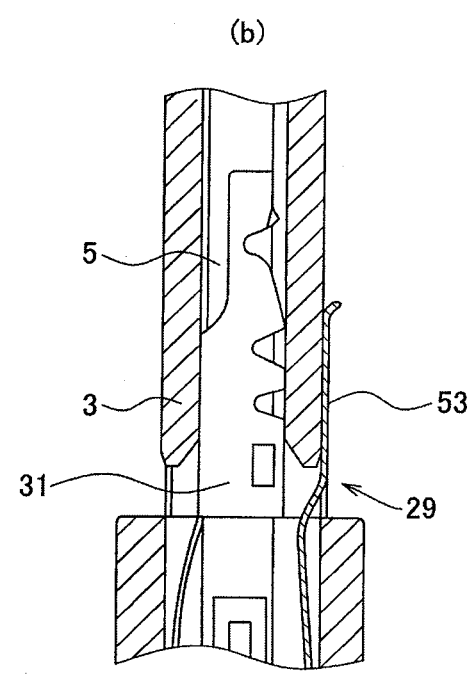

More specifically, as shown in FIG. 9, the rear intermediate assembly unit 113 is fixed to an assembling device, with the ceramic heater 5 facing upward. The front intermediate assembly unit 111 is held above the rear intermediate assembly unit 113, and then, pressed down to a given fixed position in the rear intermediate assembly unit 113 by pushing the front intermediate assembly unit 111 from above in such a manner as to insert the ceramic heater 5 into the sensor element 3, fit the inner connection terminal 31 into the sensor element 3 and, at the same time, fit the outer connection terminal 29 onto the rear end portion of the sensor element 3.

Simultaneously with the above pressing operation, a front end portion of the outer tube 11 is fitted and crimped onto the rear end portion of the metal shell 7. Further, a part of the outer tube 11 corresponding in position to a center portion of the separator 27 and the grommet 33 is crimped. After that, the fitted front end portion of the outer tube 11 is subjected to laser welding. In this way, the oxygen sensor 1 is completed by combining the front and rear intermediate assembly units 111 and 113 into one.

c) As described above, the present embodiment is so structured that: the extension portion 55 of the outer connection terminal 29 is formed in such a manner as to protrude inwardly from the axially intermediate point of the outer fitting portion 53; and the pulling prevention portions 75 and 77 are formed on the rear end parts of the outer fitting portion 53 at positions adjacent to the extension portion 55 so as to prevent further pulling of the extension portion 55 into the through hole 23 by contact with the front end surface of the separator 27.

It is thus possible that, when the extension portion 55 of the outer connection terminal 29 is inserted in the through hole 23 of the separator 27 from one end thereof and pulled out from the other end of the through hole 23, the extension portion 55 can be prevented from further pulling by contact of the end parts of the outer fitting portion 53 (that is, the pulling prevention portions 75 and 77) with the front end surface of the separator 27.

Accordingly, the outer fitting portion 53 does not tilt with respect to the axial direction of the separator 27. The outer connection terminal 29 can be therefore favorably fitted onto the sensor element 3 in the subsequent process step without causing a breakage of the outer connection terminal 29.

Further, the extension portion 55 protrudes in the direction inclined inwardly with respect to the outer fitting portion 53 in the present embodiment. This allows the extension portion 55 to perform the spring function and makes it unlikely to cause a breakage of the outer connection terminal 29. This also allows the outer fitting portion 53 to be located radially outside of the extension portion 55 and makes it easier to bring the pulling prevention portions 75 and 77 into contact with the front end surface of the separator 27.

Furthermore, the position of protrusion of the extension portion 55 is located rear of the axially center position of the outer fitting portion 53 in the present embodiment. This leads to an advantage that the extension portion 55 is unlikely to interfere with fitting of the outer connection terminal 29 onto the sensor element 3. This also makes it possible to increase the amount of fitting of the outer connection terminal 29 on the sensor element 3 for stable fixing of the outer connection terminal 29 and the sensor element 3.

Second Embodiment

The second embodiment will be next described below. A description of the same parts and portions in the first and second embodiments will be omitted.

The present embodiment is different from the first embodiment in that the outer connection terminal has a different shape. The outer connection terminal of the present embodiment will be explained in detail below.

Figure 10:
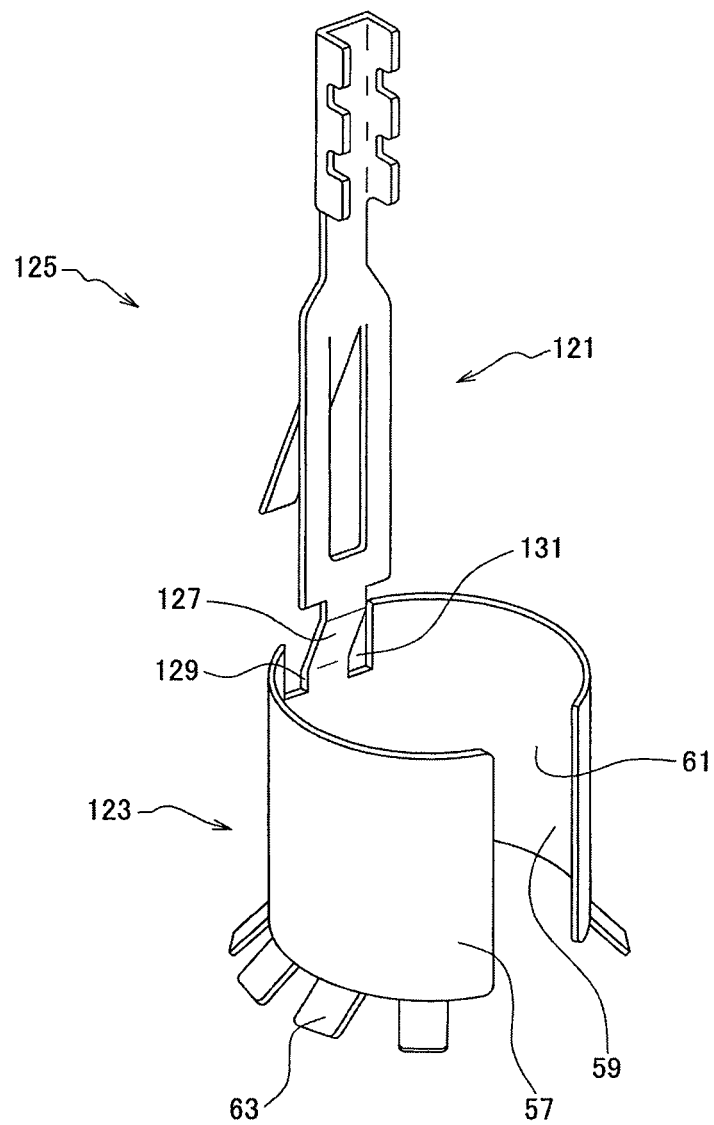
FIG. 10 is a perspective view of an outer connection terminal of an oxygen sensor according to a second embodiment of the present invention.

As in the case of the first embodiment, the outer connection terminal 121 of the oxygen sensor of the present embodiment has an outer fitting portion 123 and an extension portion 125 as shown in FIG. 10. Further, cuts 129 and 131 are formed in the outer fitting portion 123 on left and right sides of a bottom section 127 of the extension portion 125.

In the present embodiment, a lower part of the bottom section 127 extends coaxially with the outer fitting portion 123 and upwardly along an inner circumferential surface of the outer fitting portion 123; and the remaining part of the bottom section 127 extends diagonally upwardly in a direction inclined inwardly. There is also an advantage that, even if the subjected to tensile stress, a breakage is unlikely to occur in the lower part of the bottom section 127 as the lower part of the bottom section 127 is not bent relative to the outer fitting portion 123.

Although not shown in the drawings, it is feasible to modify the extension portion such that the bottom section of the extension portion protrudes inwardly perpendicular to the outer fitting portion and such that the intermediate section of the extension portion extends axially (of the outer fitting portion) perpendicular to the bottom section.

Third Embodiment

The third embodiment will be next described below. A description of the same parts and portions in the first and third embodiments will be omitted.

The present embodiment is different from the first embodiment in that the outer connection terminal has a different shape. The outer connection terminal of the present embodiment will be explained in detail below.

Figure 11:
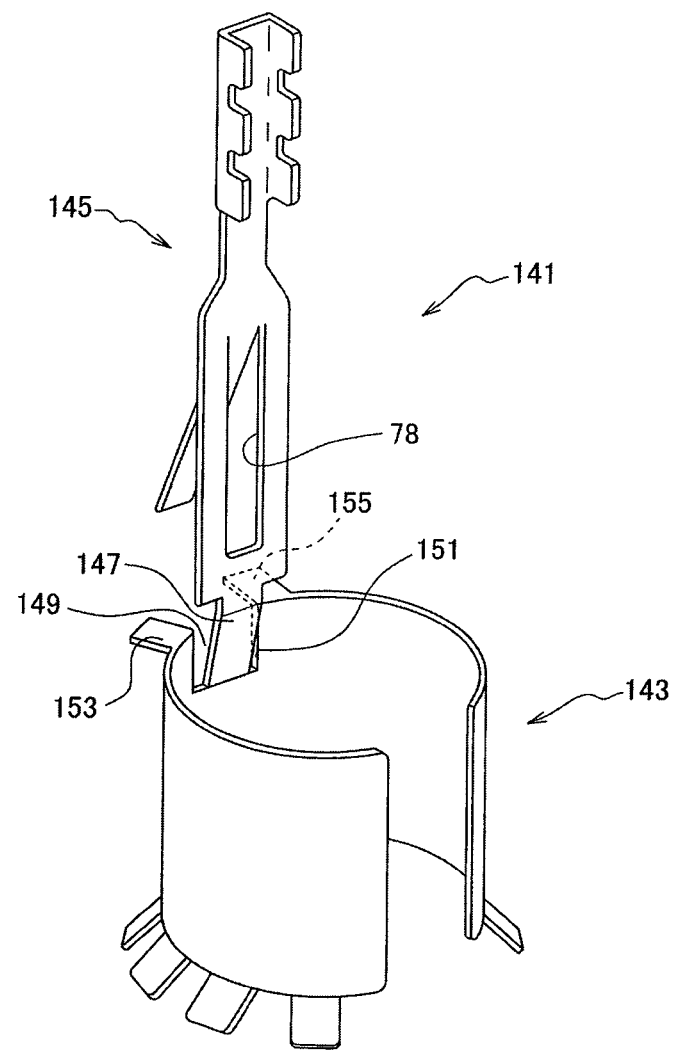
FIG. 11 is a perspective view of an outer connection terminal of an oxygen sensor according to a third embodiment of the present invention.

As in the case of the first embodiment, the outer connection terminal 141 of the oxygen sensor of the present embodiment has an outer fitting portion 143 and an extension portion 145 as shown in FIG. 11. Further, cuts 149 and 151 are formed in the outer fitting portion 143 on left and right sides of a bottom section 147 of the extension portion 145.

In the present embodiment, plate-shaped pulling prevention portions 153 and 155 are formed on upper end parts of the outer fitting portion 143 at positions adjacent to the extension portion 145 (radially adjacent to the extension portion 145 via the cuts 149 and 151) so as to protrude outwardly perpendicular to the outer fitting portion 143.

The pulling prevention portion 155 protrudes more outwardly and thereby advantageously provides a larger pulling prevention effect than that of the pulling prevention portion (constituted by the upper end part of the outer fitting portion) of the first embodiment.

Although not shown in the drawings, it is feasible to modify the extension portion such that the lower part of the bottom section of the extension portion extends coaxially with the outer fitting portion; and the remaining part of the bottom section of the extension portion extends in a direction inclined inwardly as in the case of the second embodiment.

Alternatively, it is feasible to modify the extension portion such that the bottom section of the extension portion protrudes inwardly perpendicular to the outer fitting portion.

Fourth Embodiment

The fourth embodiment will be next described below. A description of the same parts and portions in the third and fourth embodiments will be omitted.

The present embodiment is different from the third embodiment in that the outer connection terminal has a different shape. The outer connection terminal of the present embodiment will be explained in detail below.

Figure 12:
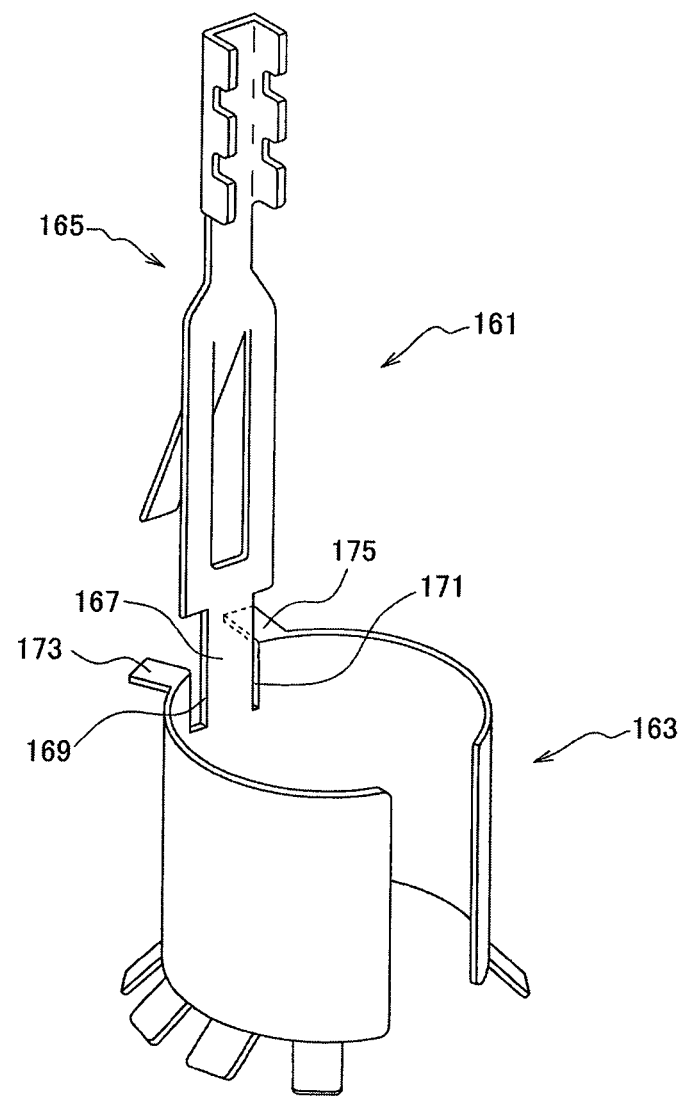
FIG. 12 is a perspective view of an outer connection terminal of an oxygen sensor according to a fourth embodiment of the present invention.

As in the case of the first embodiment, the outer connection terminal 161 of the oxygen sensor of the present embodiment has an outer fitting portion 163 and an extension portion 165 as shown in FIG. 12. Further, cuts 169 and 171 are formed in the outer fitting portion 163 on left and right sides of a bottom section 167 of the extension portion 165. Alternatively, the cuts 169 and 171 may not be formed.

In the present embodiment, the extension portion 165 extends coaxially and upwardly in the same plane as the outer fitting portion 163 (over which the inner and outer circumferential surfaces spread); and plate-shaped pulling prevention portions 173 and 175 are formed on upper end parts of the outer fitting portion 163 at positions adjacent to the extension portion 165 (radially adjacent to the extension portion 165 via the cuts 169 and 171) so as to protrude outwardly perpendicular to the outer fitting portion 163.

It is thus possible in the present embodiment to obtain the same effects as in the third embodiment.

In the case of using the outer connection terminal 161 of the present embodiment, a separator having a through hole into which the extension portion 165 of the outer connection terminal 161 can be axially straightly inserted is used in combination.

Fifth Embodiment

The fifth embodiment will be next described below. A description of the same parts and portions in the fourth and fifth embodiments will be omitted.

The present embodiment is different from the fourth embodiment in that the outer connection terminal has a different shape. The outer connection terminal of the present embodiment will be explained in detail below.

Figure 13:
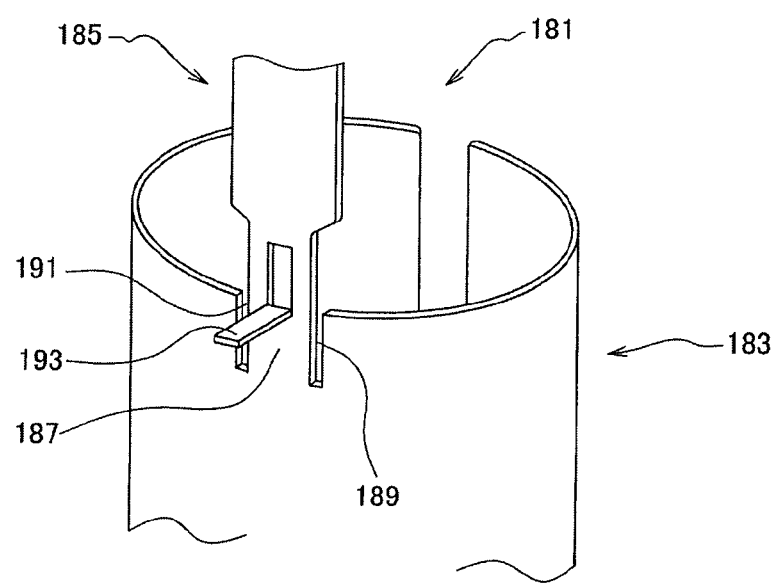
FIG. 13 is a perspective view of an outer connection terminal of an oxygen sensor according to a fifth embodiment of the present invention.
Figure 14:
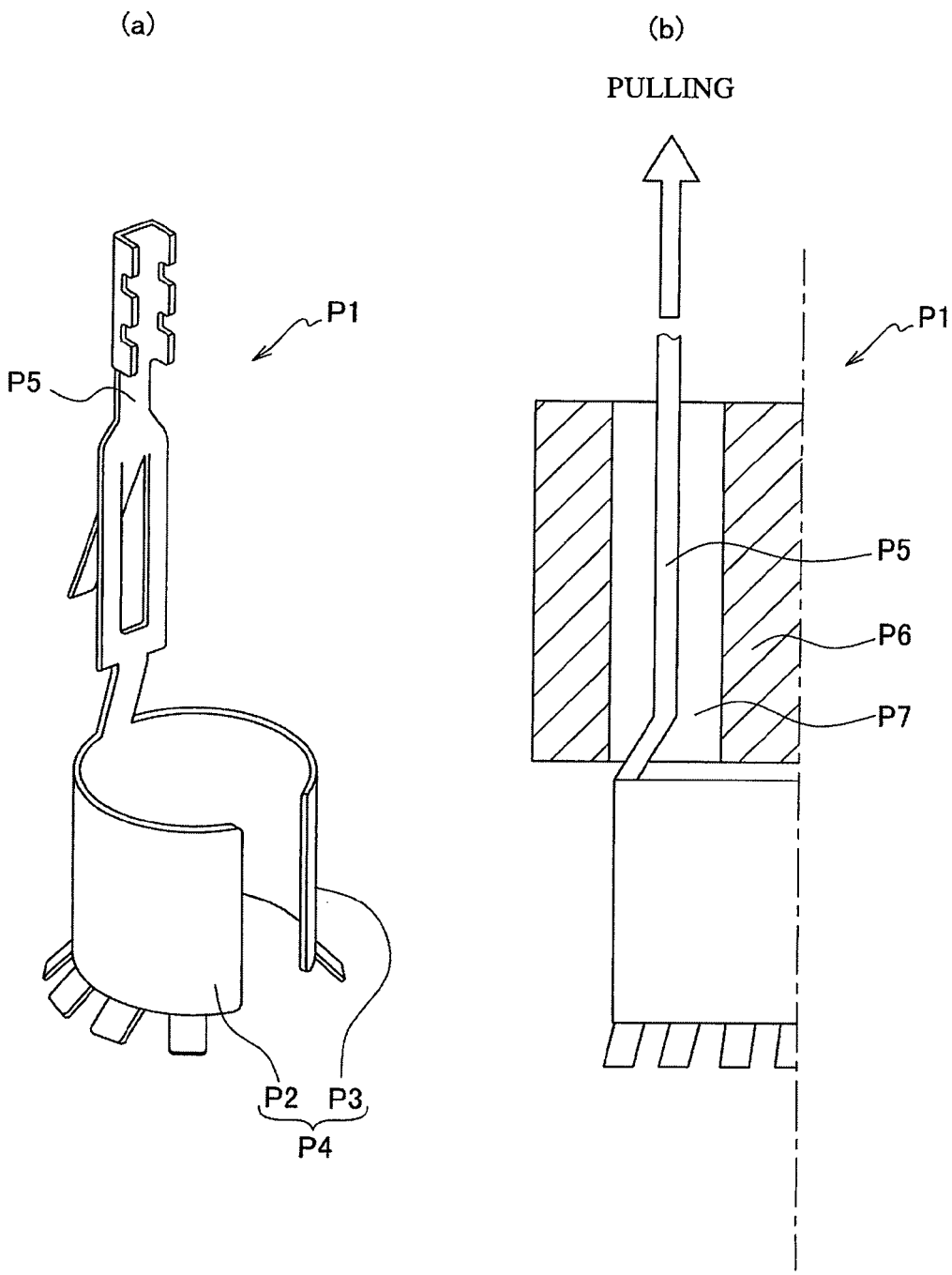
FIG. 14 is a schematic view showing a conventional technology.
Figure 15:
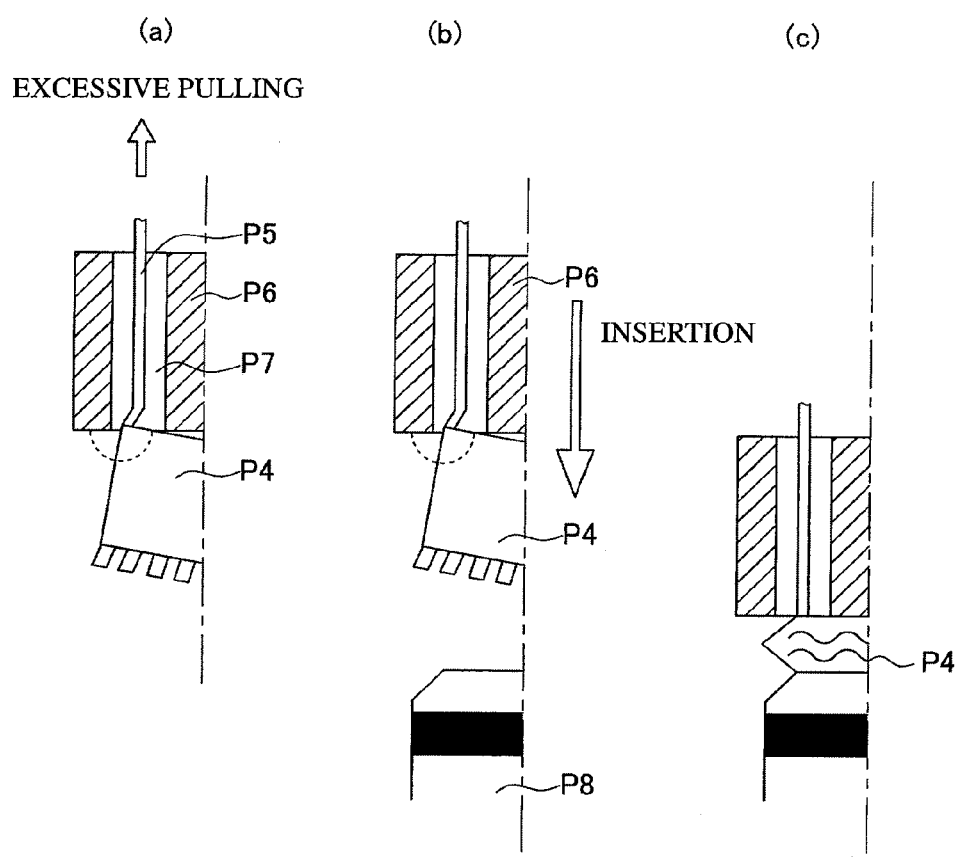
FIG. 15 is a schematic view showing problems of the conventional technology.

As in the case of the fourth embodiment, the outer connection terminal 181 of the oxygen sensor of the present embodiment has an outer fitting portion 183 and an extension portion 185 as shown in FIG. 13. Further, cuts 189 and 191 are formed in the outer fitting portion 183 on left and right sides of a bottom section 187 of the extension portion 185.

In the present embodiment, a plate-shaped pulling prevention portion 193 is formed on an outer side of the extension portion 185 and, more specifically, at the same position as an upper end of the outer fitting portion 183 on the outer side of the extension portion 185, so as to protrude outwardly perpendicular to the extension portion 185. This pulling prevention portion 193 is formed by making a U-shaped cut in the extension portion 185.

It is thus possible in the present embodiment to obtain the same effects as those in the fourth embodiment.

The present invention is not limited to the above embodiments. Various modification and variations of the above embodiments are possible within the technical scope of the present invention.

DESCRIPTION OF REFERENCE NUMERALS

1: Oxygen sensor
3: Sensor element
23, 25, 91, 93: Through hole
27: Separator
29, 121, 141, 161, 181: Outer connection terminal
53, 123, 143, 163, 183: Outer fitting portion
55, 85, 125, 145, 165, 185: Extension portion
65, 127, 147, 167, 187: Bottom section
71, 73, 129, 131, 149, 151, 169, 171, 189, 191: Cut
75, 77, 153, 155, 173, 175, 193: Pulling prevention portion

The invention claimed is:

1. A gas sensor, comprising:
a cylindrical sensor element;
a connection terminal extending axially of the sensor element and brought into contact with an outer surface of the sensor element; and
a separator located rear of the sensor element and having a through hole in which a rear end side of the connection terminal is inserted,
wherein the connection terminal has:
a cylindrical outer fitting portion formed on a front end side of the connection terminal and fitted onto the sensor element;
an extension portion extending rearward from the outer fitting portion and inserted in the through hole of the separator; and
a pulling prevention portion adapted to prevent the extension portion from further pulling in the through hole by contact with a front end surface of the separator;
wherein the outer fitting portion has cuts axially formed in a rear end side thereof such that the cuts are located on opposite sides of the extension portion; and
the extension portion includes a bottom section protruding axially from a position in front of a rear end of the outer fitting portion.

2. The gas sensor according to claim 1, wherein the pulling prevention portion is formed on a rear end part of the outer fitting portion at a position adjacent to the extension portion so as to prevent the extension portion from further pulling in the through hole by contact with the front end surface of the separator.

3. The gas sensor according to claim 1, wherein the pulling prevention portion is formed on a rear end part of the outer fitting portion at a position adjacent to the extension portion so as to protrude outwardly from the outer fitting portion and prevent the extension portion from further pulling in the through hole by contact with the front end surface of the separator.

4. The gas sensor according to claim 1, wherein the pulling prevention portion is formed on the extension portion so as to protrude outwardly from the extension portion and prevent the extension portion from further pulling in the through hole by contact with the front end surface of the separator.

5. The gas sensor according to claim 1, wherein the extension portion protrudes in a direction inclined inwardly with respect to an axial direction of the outer fitting portion.

6. The gas sensor according to claim 1, wherein the extension portion includes a part extending from the bottom section in a direction inclined inwardly with respect to the axial direction.

7. The gas sensor according to claim 1, wherein a position at which the extension portion protrudes inwardly from the outer fitting portion is located rear of an axially center position of the outer fitting portion.

8. The gas sensor according to claim 1, wherein the cuts are formed on circumferentially opposite sides of the extension portion.

9. The gas sensor according to claim 1, wherein the connection terminal further comprises a rectangular protrusion piece in the extension portion.

* * * * *